United States Patent

Wada et al.

[11] Patent Number: 5,088,326
[45] Date of Patent: Feb. 18, 1992

[54] PIEZOELECTRIC ACCELEROMETER FOR AUTOMOBILES

[75] Inventors: Shunichi Wada; Masayuki Yano, both of Himeji, Japan

[73] Assignee: Mitsubishi Denki K.K., Tokyo, Japan

[21] Appl. No.: 526,913

[22] Filed: May 22, 1990

[30] Foreign Application Priority Data

| May 24, 1989 | [JP] | Japan | 1-60711[U] |
| May 24, 1989 | [JP] | Japan | 1-60712[U] |
| Jun. 2, 1989 | [JP] | Japan | 1-65137[U] |

[51] Int. Cl.$^5$ ............................................. G01P 15/09
[52] U.S. Cl. .................................. 73/517 R; 73/431; 73/654; 310/329
[58] Field of Search ............... 73/517 R, 654, 431, 73/493, 497; 310/315, 319, 329

[56] References Cited

U.S. PATENT DOCUMENTS

| 3,390,286 | 6/1968 | Gradin et al. ............... 310/319 |
| 3,400,284 | 9/1968 | Elazar ............................ 310/319 |
| 3,701,903 | 10/1972 | Merhar ........................... 310/329 |
| 4,178,525 | 12/1979 | Barr ............................... 310/329 |
| 4,463,596 | 8/1984 | Asakura .......................... 310/329 |
| 4,700,973 | 10/1987 | Gademann et al. ............... 73/431 |
| 4,816,713 | 3/1989 | Change, Jr. ..................... 310/319 |

FOREIGN PATENT DOCUMENTS 2206415 1/1989 United Kingdom .
87/05402 9/1987 World Int. Prop. O. .

*Primary Examiner*—John E. Chapman
*Attorney, Agent, or Firm*—Sughrue, Mion, Zinn, Macpeak & Seas

[57] ABSTRACT

An accelerometer for automobiles is disclosed which is mounted on an electrically insulating plate (i.e., a printed circuit board) accommodated within an electrically conductive casing. The electrical connections from the electrodes of the piezoelectric element to the inputs of the charge amplifier are effected by a wiring pattern formed on the insulating plate. The casing consists of an open box-shaped base and a plate-shaped cover, a packing member being interposed therebetween, wherein an electrical connection between the base and the cover is provided by the fixing screws for fixing the cover to the base. The cover has a central recess in which through-type capacitors for producing hermetically sealed electrical connections through a wall of the casing are accommodated. Further, the charge amplifier comprises a temperature compensating capacitor having a positive temperature coefficient of capacitance which is coupled across the electrodes of the piezoelectric element; thus, the variation of the output voltage due to the change in the ambient temperature is compensated for by the capacitor and hence is reduced.

11 Claims, 4 Drawing Sheets

A: VAR. RATE OF kr
B: VAR. RATE OF √C
C: COMP. VAR. RATE OF A & B

D: VAR. RATE OF fr
E: VAR. RATE OF $C_i$
F: COMP. VAR. RATE OF D & E

G: COMP. VAR. RATE OF C & F

PIEZOELECTRIC ACCELEROMETER FOR AUTOMOBILES

BACKGROUND OF THE INVENTION

This invention relates to piezoelectric accelerometers, and especially to piezoelectric accelerometers for detecting the vibrations or the degree of riding comfort of automotive vehicles.

Piezoelectric accelerometers are used conventionally for detecting the vibrations or the degree of riding comfort of automotive vehicles. Let us first describe the overall organization of a peizoelectric accelerometer by reference to FIG. 1, which, by the way, shows the fundamental organization of an accelerometer according to this invention.

In FIG. 1, within an electrically conductive casing 1 is accomodated an electrically insulating plate 9, on which a weight 2 and a piezoelectric element 4 are attached by means a fixing screw 5, extending through the weight 2 and the element 4, and a nut 15 engaing with the screw 5. The insulating plate 9 consists of a printed circuit board made of an epoxy resin or a ceramic. The piezoelectric element 4, disposed between its upper and lower electrodes 3a and 3b, is secured to the casing 1 via the insulating plate 9. The lower electrode 3b bears on the plate 9, while the upper electrode 3a is held between the weight 2 and the piezoelectric element 4; the electrodes 3a and 3b are electrically coupled via the respective output leads 13 and 14 of the piezoelectric element to the input terminals of a charge amplifier 6.

The charge amplifier 6, mounted to the electrically insulating plate 9, pre-amplifies the detector output signal of the piezoelectric element 4. The charge amplifier 6 is utilized for the purpose of reducing the adverse effects of the noises and of the variations in the voltage source level. An amplifer 7, also mounted on the insulating plate 9, amplifies the output of the charge amplifier 6. The output terminal of the amplifier 7 is electrically coupled, via a three-terminal capacitor 8b, a through type capacitor 10b, and a lead 33, to the input terminal of a control device 11.

A stabilizing voltage source 12, comprising a stabilizing voltage source circuit (not shown) of the control device 11, supplies a source voltage to the piezoelectric accelerometer via a voltage supply lead 31, a through-type capacitor 10a, and a three-terminal capacitor 8a. The grounded negative terminal of the stabilizing voltage source 12 is coupled to the electrically conductive casing 1 via a grounding lead 32. Further, the casing 1 is coupled via the grounding lead 16 to the insulating plate 9. Thus, the grounding of the electronic circuits on the insulating plate 9 is effected by means of electrical connections to the casing 1 and thence to the grounding lead 32 of the control device 11, the electronic circuit of the accelerometer being completely enclosed within the electrically conductive casing 1; this provides the shielding effect for the electronic circuit of the accelerometer accomodated within the casing and hence is effective in supressing the adverse effects of the external noises thereon.

The conventional piezoelectric accelerometer, however, suffers from the problem of a low assembling efficiency. Namely, the electrical connections between the charge amplifier 6 and the electrodes 3a and 3b of the piezoelectric element 4 are made by means of the leads 13 and 14; this is a difficult and time consuming process. In addition, the steps for providing electrical shielding and waterproofing of the casing 1 add to the time and labor required for completing the assembling process. A further disadvantage of the piezoelectric accelerometer results from the fact that the electrical characteristics of the piezoelectric element 4 and those of the circuit elements of the charge amplifier 6, etc., are temperature dependent and vary with temperature. Namely, changes in the ambient temperature bring about changes in the electrostatic capacity of the piezoelectric element 4 and in the electrical characteristics of the circuit elements of the charge amplifier 6, etc. Hence, the detector output voltage of the accelomter corresponding to one and the same acceleration varies with the changing ambient temperature; that is, temperature change results in the generation of error in the detector output voltage of the accelerometer.

SUMMARY OF THE INVENTION

It is therefore an object of this invention to provide a piezoelectric accelerometer which can be assembled easily with less labor and time.

In particular, this invention aims at providing a structure of the piezoelectric accelerometer according to which the electrical connections between the piezoelectric element and the charge amplifier can be made easily in the assembling process.

Further, this invention aims at providing a structure of the piezoelectric accelerometer which is capable of enhancing the assembling efficiency without impairing the shielding effect and the waterproofing performance of the electrically conductive casing.

A further object of this invention is to provide a piezoelectric accelerometer whose detection accuracy is not seriously affected by the change in the ambient temperature. Since the ambient temperature changes are substantial in the case of the accelerometer for automobiles, the compensation and the reduction of the output error caused by temperature changes is important.

The accelerometer according to this invention comprises: a closed box-shaped electrically conductive casing which is grounded; an electrically insulating plate disposed within said electrically conductive casing and having a wiring pattern formed thereon; piezoelectric element means, mounted on the electrically insulating plate and including a piezoelectric element, a pair of electrodes holding the piezoelectric element therebetween, and a weight, for generating across the piezoelectric element a voltage corresponding to an acceleration in response to a force acting on the piezoelectric element from the weight in accordance with the acceleration; and a charge amplifier circuit means, mounted on the electrically insulating plate and having input terminals electrically coupled to said electrodes, for amplifying the voltage generated across the piezoelectric element; wherein the electrodes of the piezoelectric element means are electrically coupled to input terminals of the charge amplifier via the wiring pattern formed on the electrically insulating plate. It is preferred that each electrode of the piezoelectric element comprises an extension whose bent end is soldered to a terminal of a wiring of the wiring pattern on the electrically insulating plate, which wiring being electrically coupled to an input terminal of the charge amplifier. Thus, the assembling efficiency is enhanced.

The electrically conductive casing is preferred to comprise: an open box-shaped base portion made of an electrically conductive material and accomodating the electrically insulating plate; a plate-shaped cover portion of electrically conductive material closing an opening of the open box-shaped base portion; an electrically non-conductive sealing member interposed between the base portion and the cover portion to ensure a hermetical sealing between the base portion and the cover portion of the electrically conductive casing; and fixing means for fixedly attaching the cover portion to the base portion, the fixing means including electrical conduction means for securing electrical connection between the cover portion and the base portion of the electrically conductive casing. The sealing member may comprise a ring-shaped packing member, and the fixing means may comprise fixing screws extending through the packing member and made of an electrically conductive material which provide electrical connection between the base portion and the cover portion of the electrically conductive casing. Further, the accelerometer is preferred to comprise through-type capacitors mounted to the electrically conductive casing so as to provide hermetically sealed electrical connections through a wall of the electrically conductive casing between an external circuit situated outside the electrically conductive casing and an electronic circuit of the accelerometer situated within the electrically conductive casing, wherein said cover portion of the electrically conductive casing has a recess formed on an outward surface thereof, the through-type capacitors being mounted to a side wall of the recess so that the through-type capacitors are accomodated within the recess. Thus, the assembling efficiency is enhanced without impairing the shielding effect and the waterproofing performance of the casing.

On the other hand, it is preferred that the charge amplifier circuit means comprises a capacitor having a positive temperature coefficient of capacitance coupled across the electrodes of the piezoelectric element means, the capacitor providing a temperature compensation for a variation of output voltage of the accelerometer caused by a change in an ambient temperature. Generally, the charge amplifier circuit means further comprises a resistor coupled in parallel with the capacitor and an operational amplifier circuit configuration having two inputs coupled across the the parallel circuit of the capacitor and the resistor.

BRIEF DESCRIPTION OF THE DRAWINGS

The novel features which are believed to be characteristic of this invention are set forth with particularity in the appended claims. This invention itself, however, both as to its organization and method of operation, together with further objects and advantages thereof, may be best understood by reference to the following detailed description of the preferred embodiment, taken in connection with the accompanying drawings, in which:

In the drawings, like reference numerals represent like or corresponding parts.

DETAILED DESCRIPTION OF THE PREFERRED EMBODIMENT

Referring now to FIGS. 1 through 6 of the drawings, let us describe an embodiment of this invention.

Figure 1:
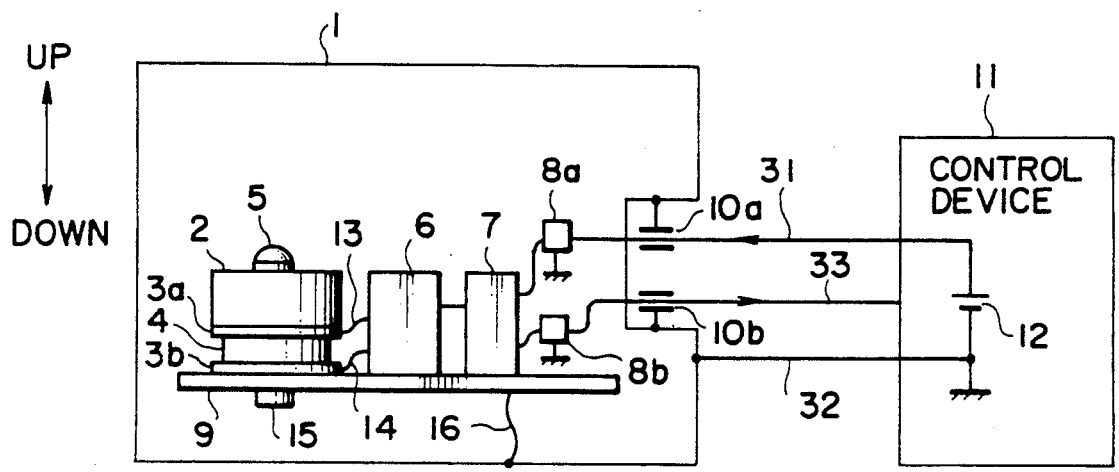
FIG. 1 is a schematic sectional side view of the accelerometer according to this invention, showing an overall organization thereof.

FIG. 1 shows the overall organization of a piezoelectric accelerometer for automobiles according to this invention. The overall organization of the accelerometer is the same as that described above by reference to FIG. 1, except for the details specifically described hereinbelow. Thus, for the description of the overall organization of the accelerometer, reference is to be made to the description above. It is to be noted in FIG. 1, however, that the electrically conductive casing 1, coupled to the ground via the grouding lead 32, is electrically coupled (via the grounding lead 16 in FIG. 1) to the grounding leads of the electronic circuit on the electrically insulating plate 9; thus, the electronic circuits on the insulating plate 9 are protected by the shielding effect provided by the electrically conductive casing 1, and hence the adverse effects thereon of the external noises are effectively suppressed.

Figure 2:
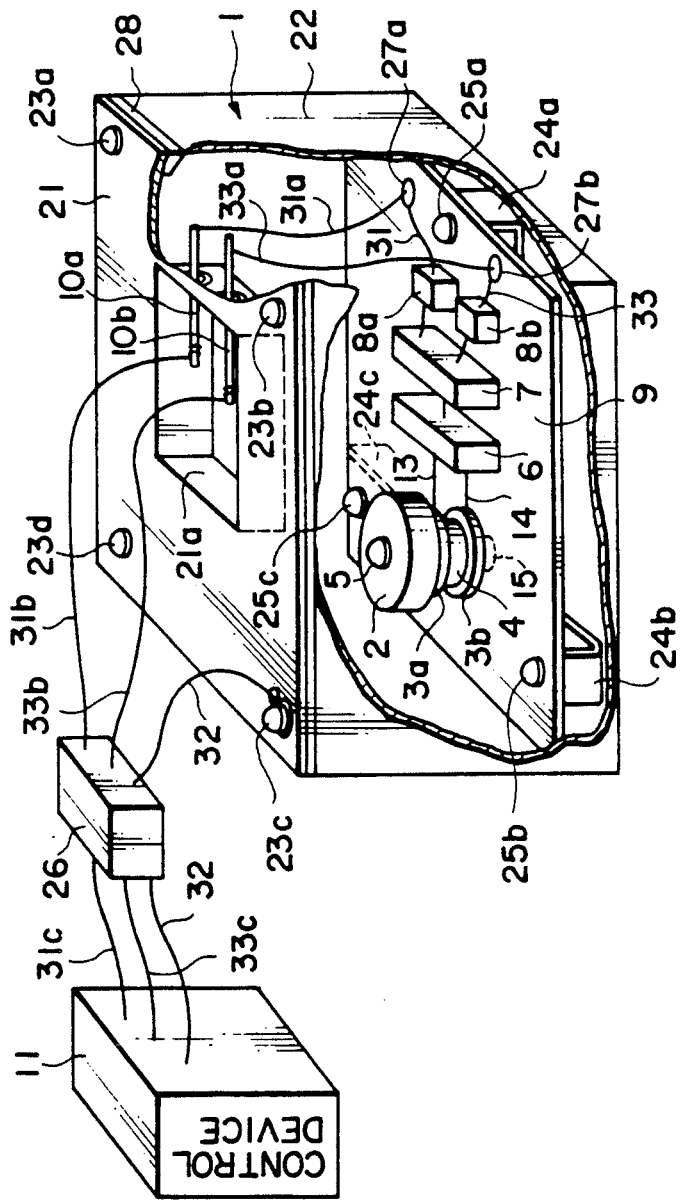
FIG. 2 is a perspective partially cutaway view of the accelerometer according to this invention, showing the configuration within the electrically conductive casing thereof.

Referring next to FIG. 2, let us describe the interior configuration of the accelerometer within the electrically conductive casing 1.

The electrically conductive casing 1 comprises a rectangular box-shaped base portion 22 and a plate-shaped cover 21 (whose structure is described in detail hereinbelow) secured to the base portion 22 by means of fixing screws 23a, 23b, 23c, and 23d. A rectangular ring-shaped packing (or sealing) member 28, made, for example, of a synthetic rubber or resin, is interposed between the base 22 and cover 21, both made of an electrically conductive material, for ensuring waterproof mounting connection of the cover 21 to the base 22 of the electrically conductive casing 1; the electrical connection between the cover 21 and the base 22 of the electrically conductive casing 1 is ensured by means of the fixing screws 23a through 23d that are made of an electrically conductive material.

As also shown in FIG. 2, the electrically insulating plate 9, made, for example, of an epoxy resin or a ceramic, is secured by means of fixing screws 25a through 25c to a plurality of spacer members 24a through 24c, which spacer members are secured to the bottom of the base portion 22 of the casing 1. Thus, the grounding electrical connections of the electronic circuits on the electrically insulating plate 9 are effected by means of the screws 25a through 25c and the spacers 24a through 24c, which are electrically connected to the casing 1.

Figure 3:
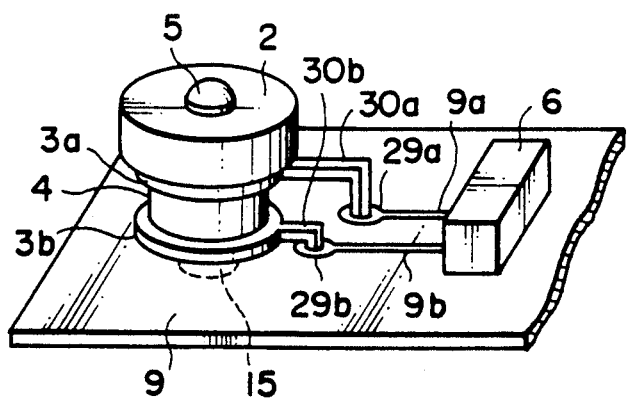
FIG. 3 is a partial perspective view of the electrical insulating plate of the accelerometer of FIG. 2, showing the electrical connections between the electrodes of the piezoelectric element and the charge amplifier.

The upper and lower electrodes 3a and 3b of the piezoelectric element 4 are coupled, as shown in FIG. 2, via the lead 13 and 14 to the two input terminals of the charge amplifier 6. The detailed structure of the leads 13 and 14 is shown in a perspective view in FIG. 3. As shown in FIG. 3, the upper and lower electrodes 3a and 3b of the piezoelectric element 4 each comprise an integrally formed extension 30a and 30b; the downward directed respective ends of the extensions 30a and 30b of the electrodes 3a and 3b are soldered to round electrodes 29a and 29b, respectively, which are formed at the ends of printed circuit wirings 9a and 9b, respectively, formed on the plate 9. The circuit wirings 9a and 9b on the plate 9 are soldered and thus electrically coupled to the input terminals of the charge amplifier 6. The lead 13 as represented in FIG. 2 consists of the extension 30a, the round 29a, and the wiring 9a; the lead 14, of the extension 30b, round 29b, and the wiring 9b. Thus, the electrical connection from the electrodes 3a and 3b of the piezoelectric element 4 to the charge amplifier 6 can be effected easily by soldering the extensions 30a and 30b of the electrodes 3a and 3b to the rounds 29a and 29b of the printed wirings 9a and 9b during the assembly process of the accelerometer. This greatly improves the efficiency of the assembling step. Incidentally, the circuit organization of the charge amplifier 6 is described in detail hereinbelow by reference to FIG. 4.

As shown in FIG. 2, the output terminal of the charge amplifier 6 is coupled to the input terminal of an amplifier 7 mounted on the insulating plate 9. The voltage supply lead 31 and the output lead 33 of the amplifier 7 are elecrically coupled via the three-terminal capacitors 8a and 8b to the round terminals 27a and 27b, respectively, which rounds are formed on the electrically insulating plate 9. These three-terminal capacitors 8a and 8b serve as noise filters. The rounds 27a and 27b are coupled via the leads 31a and 33a, respectively, to the inner terminals of the respective through-type capacitors 10a and 10b, the other (i.e., outer) terminals of the through-type capacitors 10a and 10b being coupled via the leads 31b and 33b to the connector 26, and thence to the control device 11 via the leads 31c and 33c, respectively. The electrical connection of the leads 31, 33, 31a and 33a to the rounds 27a and 27b, or that of the leads 31a, 33a, 31b, and 31bto the respective terminals of the through-type capacitors 10a and 10b are effected by the soldering step. The grounding lead 32 of the control device 11 is coupled via the connector 26 to the cover 21 of the casing 1, wherein the end of the grounding lead 32 at the electrically conductive casing 1 is secured to the upper surface of the cover 21 by means of the head of the fixing screw 23c. Thus, the casing 1 is grounded via the grounding lead 32, thereby providing a shielding effect to the electronic circuits of the accelerometer accomodated therein.

As shown clearly in FIG. 2, the cover portion 21 of the casing 1 comprises a rectangular recess 21a formed on the upper surface thereof so as to accomodate the through-type capacitors 10a and 10b therein. The through-type capacitors 10a and 10b are soldered and thus attached to a side wall of the recess 21a; thus, the capacitors 10a and 10b are completely accomodated within the recess 21a of the cover 21, so that no projections are formed on the upper surface of the cover 21 of the casing 1. This accomodation of the through-type capacitors 10a and 10b within the recess 21a of the cover 21 of the casing 1 has the following advantage in addition to the obvious one of eliminating projections situated outside the casing 1. Namely, since the through-type capacitors 10a and 10b are attached to the cover 21 which is separate from the base 22 before the assembling of the accelerometer is effected, the efficiency of the soldering process of the through-type capacitors 10a and 10b can be improved. Further, also since the capacitors 10a and 10b are mounted to the cover 21, the soldering of the leads 31a and 33a (already soldered to the respective terminals of the capacitors 10a and 10b) to the rounds 27a and 27b on the plate 9 can be effected before the plate 9 is mounted to the base portion 22 of the casing 1. This also contributes to enhancing the assembling efficiency. It is further noted that since the cover 21 of the casing 1 is mounted to the base portion 22 thereof via the packing member 28 and since the through-type capacitors 10a and 10b are soldered to the cover without any gaps or openings between the cover 21 and the capacitors 10a and 10b, the air-tightness and waterproofing of the electrically conductive casing 1 is enhanced.

Figure 4:
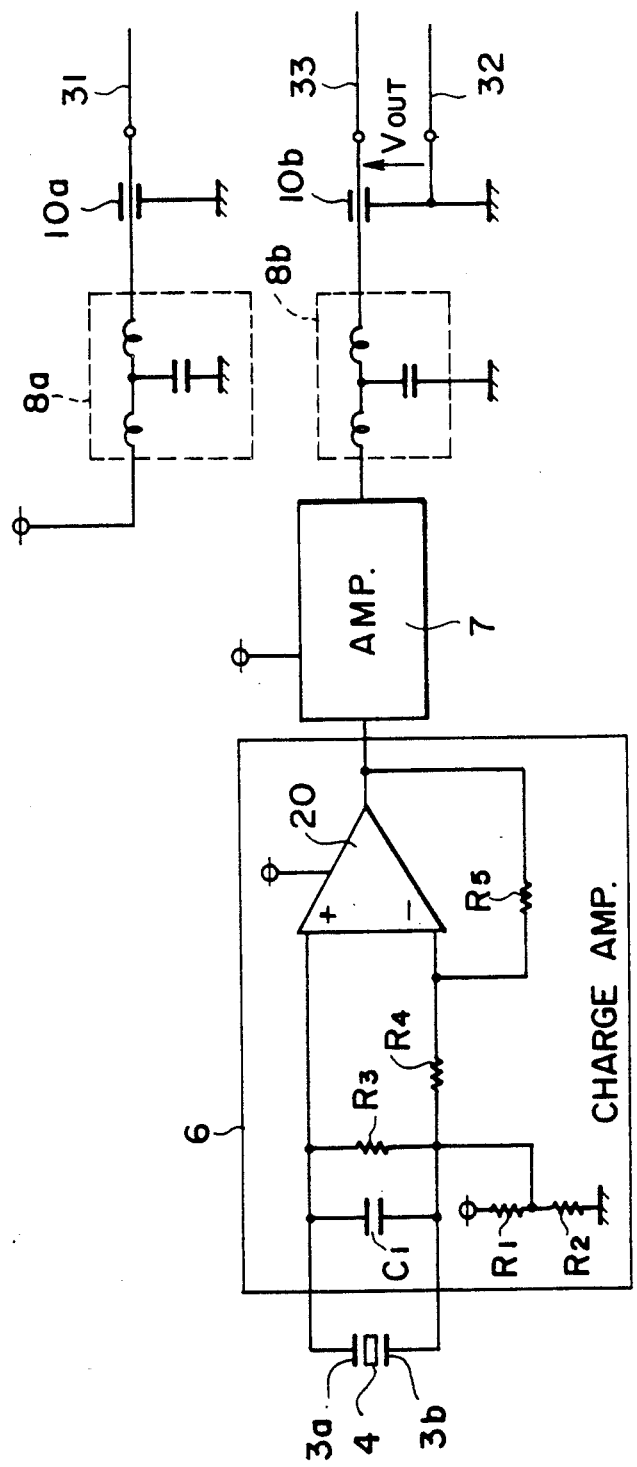
FIG. 4 is a circuit diagram showing the circuit organization of the charge amplifier of the accelerometer according to this invention.

Referring next to FIG. 4 of the drawings, let us describe the circuit organization of the accelerometer according to this invention.

In FIG. 4, the charge amplifier 6 comprises a capacitor C1 and a resistor R3 coupled in parallel circuit relationship across the upper and lower electrodes 3a and 3b of the piezoelectric element 4, wherein the terminal of the resistor R3 coupled to the electrode 3b is coupled to an intermediate point of the voltage divider consisting of serially connected resistors R1 and R2, which voltage divider is coupled across the voltage source and the ground. Thus, the potential of the electrode 3b is maintained to a predetermined level with respect to the ground that is determined by the voltage level of the source and the resistance ratio of the voltage divider resistors R1 and R2. Further, the non-inverting (+) input of an operational amplifier 20 having a FET (field effect transistor) input configuration is coupled to the upper electrode 3a of the piezoelectric element 4, while the inverting (−) input of the amplifier 20 is coupled to the lower electrode 3b of the piezoelectric element 4 via an input resistor R4 thereof. Further, the output of the operational amplifier 20 is coupled via a feedback resistor R5 thereof to the inverting input thereof. It is noted that the closed loop gain of this inverting amplifier configuration of the operational amplifier 20 is determined by the ratio of the feedback resistance R5 to the input resistance R4. It is further noted that the charge amplifier 6 comprises the capacitor C1, resistors R1 through R5, and the operational amplifier 20.

It is to be noted in the above circuit organization of the charge amplifier 6 that the non-inverting and inverting inputs of the operational amplifier 20 having FET input configuration are coupled to each other via the resistor R3, so that the potentials of both inputs of the operational amplifier 20 vary simultaneously in an interlocked manner when the supply voltage varies; thus, the adverse effects of the variation in the supply voltage is reduced. On the other hand, the capacitor C1 is inserted in the circuit so as to increase the time constant of the input circuit portion of the charge amplifier 6, thereby reducing the minimum frequency of acceleration detected by the accelerometer. Further, as described in detail hereinbelow, the capacitor C1 has a positive temperature characteristic so as to minimize the detector output voltage variation caused by the variation in the ambient temperature.

Further, the output of the operational amplifier 20, constituting the output of the charge amplifier 6, is amplified by the amplifier 7, and is outputted via the three-terminal capacitor 8b and the through-type capacitor 10b to the output lead 33. In addition, the voltage supply to the charge amplifier 6 and to the amplifier 7 is coupled via the three-terminal capacitor 8a and the through-type capacitor 10a to the voltage supply lead 31.

The output voltage Vout of the accelerometer circuit (see FIG. 4), which is generated across the leads 33 and 32 when a force F is applied on the piezoelectric element 4, is expressed by the following equation:

$$V_{out} = \alpha(\sqrt{C} \cdot kr/fr \cdot C1) \cdot F \cdot (1 + R5/R4) \cdot K \quad (1)$$

wherein:
α is a constant,
fr is the resonant frequency,
kr is the coupling coefficient,
C1 is the electrostatic capacitance of the capacitor C1,
C is the electrostatic capacitance of the piezoelectric element,
F is the force acting on the piezoelectric element,
K is the gain of the amplifier 7, and
R4 and R5 are the resistance values of the input and feedback resistors R4 and R5, respectively, of the charge amplifier 6.

Let us now describe the operation of the charge amplifier 6 so as to make clear the respective factors appearing in the above equation (1).

When the force resulting from the acceleration of the weight 2 acts on the piezoelectric element 4, a voltage corresponding to the acceleration is developed across the electrodes 3a and 3b due to the polarization of the piezoelectric element 4 corresponding to the acceleration. This voltage developed across the electrodes 3a and 3b is expressed by:

$$\alpha \cdot (\sqrt{C} \cdot kr)/(fr \cdot C1), \quad (2)$$

which appears as a factor of the above equation (1); this voltage is applied across the input terminals of charge amplifier 6. More precisely, the above voltage (2) corresponding to the acceleration is applied across the inputs of the inverting circuit configuration of the operational amplifier 20 having the input and feedback resistors R4 and R5, to be thus amplified by the voltage amplification factor (or voltage gain) determined by the ratio of R5 to R4:

(1+R5/R4).

The output of the operational amplifier 20 is further amplified by the amplifier 7 by a voltage gain equal to K, to be outputted to the output lead 33 of the accelerometer via the three-terminal capacitor 8b and the through-type capacitor 10b. Thus, the output voltage Vout of the accelerometer is expressed by the equation (1) above.

Since the temperature coefficient of the resistance of resistors are generally small, the variation due to temperature variation of the gain or amplification factor determined by the R5 and R4:

(1+R5/R4)

obtained by means of the inverting circuit configuration of the operational amplifier 20 with the input and feedback resistors R4 and R5 is small and hence can be neglected in the consideration of the variation of the output voltage Vout given by the equation (1). Thus, the variation of the output voltage Vout caused by the temperature variation is determined by the temperature coefficient of the factor:

$$\sqrt{C} \cdot kr/fr \cdot C1. \quad (2')$$

Namely, the temperature variation of the output voltage Vout is determined for the main part by the temperature characteristics of the factor given by (2').

Figure 5A:
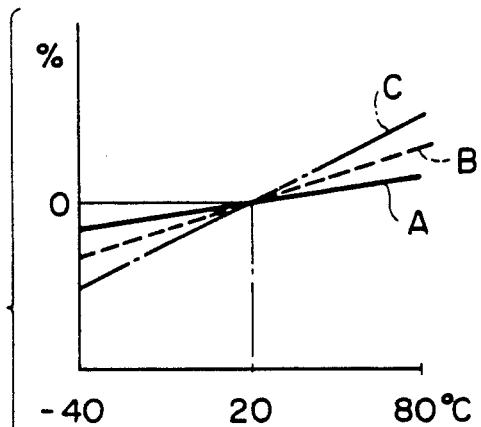
FIGS. 5 (a) through (c) are diagrams showing the variation rates (with respect to temperature plotted along the abscissae) of various factors affecting the output voltage of the accelerometer.
Figure 5B:
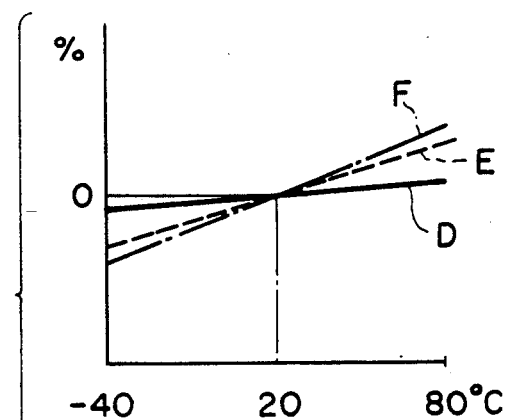
Figure 5C:
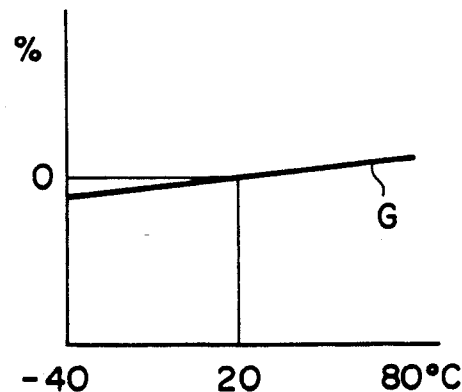

FIG. 5 (a) shows the variation rates (plotted along the ordinates in percent), with respect to ambient temperature (plotted along the abscissas), of the coupling coefficient kr (solid line A), and the square root of the capacitance C of the piezoelectric element 4 (dotted line B); thus, the variation rate of the composition (or product) of the coupling coefficient kr and the square root of the capacitance C of the piezoelectric element 4, which composition appears as the numerator in the expression (2') above, takes the form as represented by solid line C. On the other hand, FIG. 5 (b) shows the variation rate with respect to temperature of the resonance frequency fr (solid line D) and the capacitance C1 (dotted line E); thus, the variation rate of the composition (or product) of the resonance frequency fr and the capacitance C1, which composition appears as the denominator in expression (2') above, takes the form as represented by the solid line F. Hence, the variation rate of the composition (or quotient) of the values as represented by the curves C and F, which composition or quotient corresponds to the whole expression (2') above, takes the form as represented by the solid line G in FIG. 5 (c).

Thus, according to this invention, the variation rate E with respect to the temperature of the capacitor C1 coupled across the electrodes 3a and 3b of the piezoelectric element 4 is selected such that the composite variation rate F of the denominator of the expression (2') becomes approximately equal to the composite variation rate C of the numerator in the expression (2'). Namely, according to this invetion, the capacitance of the capacitor C1 has a positive temperature characteristic (i.e., positive temperature coefficient) of a predetermined magnitude such that the composite variation rate C of the coupling coefficient kr and the square root of the capacitance C of the piezoelectric element 4 is approximately equal to the composite variation rate F of the resonant frequency fr and the capacitiance C1. By this measure, the final composite variation rate G with respect to the temperature of the whole expression (2') can be rendered to have a moderate characteristic (i.e., the value of G can be confined within a small range around zero); thus, according to this invention, an accelerometer whose accuracy is unaffected by the temperature variation can be obtained.

It is to be noted, by the way, that if sufficient compensation of the temperature characteristic cannot be obtained solely by the positive temperature characteristic of the capacitor C1, further improvement in the temperature characteristic of the accelerometer can be obtained by giving a compensating temperature characteristic to the factor: (1+R5/R4) in equation (1) above. In such case, a thermal resistor having a positive temperature coefficient of resistance is utilized as the resistor R4; alternatively, a thermal resistor having a negative temperature coefficient of resistance (a thermistor) is utilized as the resistor R5. It is further noted that a thermal resistor can be utilized in the circuit of the amplifier 7 with the same temperature compensation effect.

In the above, description has been made of the particular embodiment of this invention. However, it would be apparent to those skilled in the art that many modifications may be made without departing from the spirit thereof, and the appended claims are contemplated to cover any such modifications as fall within the true spirit and scope of this invention.

What is claimed is:

1. An accelerometer comprising:

a closed box-shaped electrically conductive casing which is grounded;

an electrically insulating plate disposed within said electrically conductive casing and having a wiring pattern formed thereon;

piezoelectric element means, mounted on the electrically insulating plate and including a piezoelectric element, a pair of electrodes holding the piezoelectric element therebetween, and a weight, for generating a voltage across the piezoelectric element corresponding to an acceleration in response to a force acting on the piezoelectric element from acceleration of the weight; and charge amplifier circuit means, mounted on the electrically insulating plate and having input terminals electrically coupled to said electrodes, for amplifying the voltage generated across the piezoelectric element;

wherein the electrodes of the piezoelectric element means are electrically coupled to input terminals of the charge amplifier circuit means via the wiring pattern formed on the electrically insulating plate, and wherein each of said electrodes comprises an extension whose bent end is soldered to a terminal of a wiring of the wiring pattern on the electrically insulating plate, which wiring is electrically coupled to an input terminal of the charge amplifier circuit means.

2. An accelerometer as claimed in claim 1, wherein said electrically conductive casing comprises:

an open box-shaped base portion made of an electrically conductive material and accomodating the electrically insulating plate;

a plate-shaped cover portion of electrically conductive material closing an opening of the open box-shaped base portion;

an electrically non-conductive sealing member interposed between the base portion and the cover portion to provide a hermetic seal between the base portion and the cover portion of the electrically conductive casing; and fixing means for fixedly attaching the cover portion to the base portion, the fixing means including electrical conduction means for providing an electrical connection between the cover portion and the base portion of the electrically conductive casing.

3. An accelerometer as claimed in claim 2, wherein said sealing member comprises a ring-shaped packing member, and said fixing means comprises fixing screws made of an electrically conductive material extending through the packing member, said fixing screws providing said electrical connection between the base portion and the cover portion of the electrically conductive casing.

4. An accelerometer as claimed in claim 2, further comprising through-type capacitors mounted to the electrically conductive casing so as to provide hermetically sealed electrical connections through a wall of the electrically conductive casing between an external circuit situated outside the electrically conductive casing and an electronic circuit of the accelerometer situated within the electrically conductive casing, wherein said cover portion of the electrically conductive casing has a recess formed on an outward surface thereof, the through-type capacitors being mounted to a side wall of the recess so that the through-type capacitors are accomodated within the recess.

5. An accelerometer as claimed in claim 4, wherein said through-type capacitors comprise: a through-type capacitor electrically inserted in an output lead electrically connecting to an exterior circuit an output terminal of the electronic circuit of the accelerometer situated within the electrically conductive casing; and a through-type capacitor electrically inserted in a voltage supply lead for supplying a source voltage from an exterior source to the electronic circuit of the accelerometer situated within the electrically conductive casing.

6. An accelerometer as claimed in claim 1, wherein said charge amplifier circuit means comprises a capacitor having a positive temperature coefficient of capacitance coupled across the electrodes of the piezoelectric element means, the capacitor providing a temperature compensation for a variation of output voltage of the accelerometer caused by a change in an ambient temperature.

7. An accelerometer as claimed in claim 6, wherein said charge amplifier circuit means further comprises a resistor coupled in parallel with the capacitor and an operational amplifier circuit configuration having two inputs coupled across the capacitor and the resistor.

8. An accelerometer comprising:

a closed box-shaped electrically conductive casing which is grounded;

an electrically insulating plate disposed within said electrically conductive casing and having a wiring pattern formed thereon;

piezoelectric element means, mounted on the electrically insulating plate and including a piezoelectric element, a pair of electrodes holding the piezoelectric element therebetween, and a weight, for generating a voltage across the piezoelectric element corresponding to an acceleration in response to a force acting on the piezoelectric element from acceleration of the weight; and charge amplifier circuit means, mounted on the electrically insulating plate and having input terminals electrically coupled to said electrodes, for amplifying the voltage generated across the piezoelectric element; and a plurality of through-type capacitors mounted to the electrically conductive casing so as to provide hermetically sealed electrical connections through a wall of the electrically conductive casing between an external circuit situated outside the electrically conductive casing and an electronic circuit of the accelerometer situated within the electrically conductive casing;

wherein said electrically conductive casing comprises:

an open box-shaped base portion made of an electrically conductive material and accommodating the electrically insulating plate;

a plate-shaped cover portion of electrically conductive material closing an opening of the open box-shaped base portion;

an electrically non-conductive sealing member interposed between the base portion and the cover portion to produce a hermetic seal between the base portion and the cover portion of the electrically conductive casing; and fixing means for fixedly attaching the cover portion to the base portion, the fixing means including electrical conduction means for providing an electrical connection between the cover portion and the base portion of the electrically conductive casing, and wherein said cover portion of the electrically conductive casing has a recess formed on a outward surface thereof, the through-type capacitors being mounted to a sidewall of the recess so that the through-type capacitors are accommodated within the recess.

9. An accelerometer as claimed in claim 8, wherein said sealing member comprises a ring-shaped packing member, and said fixing means comprises fixing screws made of an electrically conductive material extending through the packing member, said fixing screws providing said electrical connection between the base portion and the cover portion of the electrically conductive casing.

10. An accelerometer comprising:
a closed box-shaped electrically conductive casing which is grounded;

an electrically insulating plate disposed within said electrically conductive casing and having a wiring pattern formed thereon;

piezoelectric element means, mounted on the electrically insulating plate and including a piezoelectric element, a pair of electrodes holding the piezoelectric element therebetween, and a weight, for generating a voltage across the piezoelectric element corresponding to an acceleration in response to a force acting on the piezoelectric element from acceleration of the weight; and charge amplifier circuit means, mounted on the electrically insulating plate and having input terminals electrically coupled to said electrodes, for amplifying the voltage generated across the piezoelectric element; and a plurality of through-type capacitors mounted to the electrically conductive casing so as to provide hermetically sealed electrical connections through a wall of the electrically conductive casing between an external circuit situated outside the electrically conductive casing and an electronic circuit of the accelerometer situated within the electrically conductive casing;

wherein the electrodes of the piezoelectric element means are electrically coupled to input terminals of the charge amplifier circuit means via the wiring pattern formed on the electrically insulating plate; and wherein said electrically conductive casing comprises:

an open box-shaped portion made of an electrically conductive material and accommodating the electrically insulating plate;

a plate shaped cover portion of electrically conductive material closing an opening of the open boxed-shaped base portion;

an electrically non-conductive sealing member interposed between the base portion and the cover portion to provide a hermetic seal between the base portion and the cover portion of the electrically conductive casing; and fixing means for fixedly attaching the cover portion to the base portion, the fixing means including electrical conduction means for providing an electrical connection between the cover portion and the base portion of the electrically conductive casing, and wherein said cover portion of the electrically conductive casing has a recess formed on a outward surface thereof, the through-type capacitors being mounted to a sidewall of the recess so that the through-type capacitors are accommodated within the recess.

11. The accelerometer as claimed in claim 10, wherein said through-type capacitors comprise:
a through-type capacitor electrically inserted in an output lead electrically connected to an exterior circuit;

an output terminal of the electronic circuit of the accelerometer situated within the electrically conductive casing; and a through-type capacitor electrically inserted in a voltage supply lead for supplying a source voltage from an exterior source to the electronic circuit of the accelerator situated within the electrically conductive casing.

* * * * *